United States Patent [19]

Pemawansa et al.

[11] Patent Number: 4,992,172

[45] Date of Patent: Feb. 12, 1991

[54] BLOTTING METHODS USING POLYALDEHYDE ACTIVATED MEMBRANES

[75] Inventors: Kariyawasam P. W. Pemawansa, Ann Arbor; Mark D. Heisler, Saline, both of Mich.; Menahem Kraus, Rehovot, Israel

[73] Assignee: Gelman Sciences, Inc., Ann Arbor, Mich.

[21] Appl. No.: 394,362

[22] Filed: Aug. 15, 1989

Related U.S. Application Data

[60] Continuation-in-part of Ser. No. 321,282, Mar. 9, 1989, which is a division of Ser. No. 96,730, Sep. 14, 1987, Pat. No. 4,824,870.

[51] Int. Cl.[5] .................... B01D 29/00; B01D 29/46; B01D 39/00
[52] U.S. Cl. ................ 210/490; 210/500.22; 210/500.27; 210/500.34; 210/500.35; 210/500.41; 210/500.42; 210/500.43; 521/53; 521/54
[58] Field of Search ............ 210/490, 500.22, 500.27, 210/500.35, 500.34, 500.41, 500.42, 500.43; 521/53, 54

[56] References Cited

U.S. PATENT DOCUMENTS

| | | | |
|---|---|---|---|
| 3,770,588 | 11/1973 | Forgione | 195/63 |
| 3,821,083 | 6/1974 | Van Leemputten et al. | 195/63 |
| 3,977,941 | 8/1976 | Vieth et al. | 195/63 |
| 4,066,512 | 1/1978 | Lai et al. | 195/127 |
| 4,229,537 | 10/1980 | Hodgins et al. | 435/177 |
| 4,279,787 | 7/1981 | Huizinga | 260/8 |
| 4,352,884 | 10/1982 | Nakashima et al. | 435/180 |
| 4,357,142 | 11/1982 | Schall, Jr. et al. | 23/230 |
| 4,361,484 | 11/1982 | Larsson et al. | 210/632 |
| 4,363,634 | 12/1982 | Schall, Jr. | 23/230 |
| 4,418,152 | 11/1983 | Hosaka et al. | 436/511 |
| 4,438,239 | 3/1984 | Rembaum et al. | 525/54.1 |
| 4,511,478 | 4/1985 | Nowinski et al. | 210/691 |
| 4,612,118 | 9/1986 | Kamiyama et al. | 210/490 |
| 4,624,923 | 11/1986 | Margel | 435/176 |
| 4,657,873 | 4/1987 | Gadow et al. | 436/532 |
| 4,661,526 | 4/1987 | Ford | 521/53 |

FOREIGN PATENT DOCUMENTS

54/131995 10/1979 Japan.

OTHER PUBLICATIONS

Y. Chen, S. Mason & R. E. Sparks, "Collagenase Immobilized on Cellulose Acetate Membranes", Biomaterial: Interfacial Phenomena and Applications, pp. 484–491, 1982.

Shlomo Margel, "Polyacrolein Microspheres", Methods in Enzymology, vol. 112, 1985, pp. 164–175.

"Soluble-Insoluble Complex of Trypsin Immobilized on Acrolein-Acrylic Acid Copolymer", Biotechnology and Bioengineering, vol. XVIII, (1976).

Primary Examiner—Morton Foelak
Attorney, Agent, or Firm—Krass & Young

[57] ABSTRACT

This invention relates to macromolecular transfers, gel electrophoresis, and blotting methods involving polyaldehyde activated microporous membranes.

6 Claims, No Drawings

BLOTTING METHODS USING POLYALDEHYDE ACTIVATED MEMBRANES

This is a continuation-in-part application of copending application, Ser. No. 321,282, filed on Mar. 9, 1989, which is a divisional application of Ser. No. 096,730, filed on Sept. 14, 1987, now U.S. Pat. No. 4,824,870 issued Apr. 25, 1989.

BACKGROUND OF THE INVENTION

This invention relates to macromolecular transfers, gel electrophoresis, and blotting methods involving polyaldehyde activated microporous membranes.

Aldehydes are highly reactive compounds which have been used in conjunction with a variety of materials, such as substrates, beads, and microspheres. In substrates, certain membranes have been chemically activated with aldehyde functional groups using methods such as oxidation.

Microporous membranes are known to be useful in the area of filtration. The traditional use of microporous membranes to filter materials has been based mainly on their physical properties, e.g., pore size, thickness, strength, etc. For example, retention by microfiltration membranes is accomplished mainly through mechanical sieving. Even in uses where the chemical properties of a membrane come into play, such as in gas separation or desalination, generally chemical bonding between the separated species and the membrane matrix is not employed.

A type of microporous membrane which is capable of reacting chemically with soluble or suspended species is the so-called "affinity membrane." Various affinity membranes are commercially available. Some, which are designed to interact specifically with only one or a few species in complicated mixtures, are improvements over traditional membranes which rely on physical separations. Examples of such highly specific interactions include antigen/antibody, hapten/antibody, apoprotein/cofactor and lectin/carbohydrate. Affinity membranes may be used in immunodiagnostic testing wherein the interaction between the antigen and antibody is particularly relevant. Thus, affinity membranes are useful in macromolecular transfers, gel electrophoresis, and blotting.

But the currently available affinity membranes have certain drawbacks. For some, shelf life is limited because the active groups are destroyed by prolonged exposure to the atmosphere. For others, binding capacity is limited. Nonspecific binding, which can lead to false positive readings, is a problem as well. Nonspecific covalent binding is typically remedied by treating the membrane with a blocking agent. However, blocking agents do not always solve the problem satisfactorily.

There are also various shortcomings in the methods for making activated membranes. For example, some of the methods are limited to certain substrates or membrane polymers. An oxidation reaction, for example, is limited to membranes such as cellulose acetate, and would not activate other commercial membranes such as polysulfone, nylon or polypropylene. Also other chemical reactions may damage the pore structure of certain species of microporous membranes. In still others, clogging of the pores may present a problem.

The drawbacks and shortcomings mentioned above illustrate some of the unsatisfactory characteristics of currently available affinity membranes and the need for further improvements in the art.

SUMMARY OF THE INVENTION

In a broad aspect, the present invention is directed to a blotting composition, comprising a substrate applied to an activated microporous membrane. The membrane polymer is physically activated with a mixture containing polyaldehyde. A sufficient amount of polyaldehyde is combined with the membrane polymer to provide for effective covalent bonding with amine-containing materials and other aldehyde reactive materials.

In another broad aspect, this invention is directed to a method of transferring biological samples comprising bacteria or macromolecules to an immobilizing matrix, such as a microporous membrane. The invention is also directed to a method for identifying a macromolecule, such as specific nucleic acid sequences, using a blotting matrix. In a more specific aspect, the present invention is directed to gel blotting, comprising the use of an activated microporous membrane that comprises a membrane polymer and a polyaldehyde. In still another specific aspect, the invention is directed to a dot blot method. In yet another aspect, the invention is directed to colony hybridization.

The membrane of this invention is believed to enjoy certain advantages over other membranes. Generally, the membranes of the present invention are more stable and require shorter exposure times during blocking. In some cases, the membranes of the present invention do not require reblocking prior to each new rehybridization probing. This enables a researcher to more effectively conduct research with a membrane having increased sensitivity, low liquid loss, and non-specific adsorption. Certain invention membranes are also less vulnerable to moisture, oxygen, and other operating conditions typically present in blotting.

Various membranes of the present invention demonstrate excellent binding capacity, specificity and sensitivity. Without being bound to any particular theory, the effective binding capacity of the present membrane is believed to be due in part to the aldehyde functional groups which are attached to both the inner and outer surfaces of the microporous membrane. "Sensitivity" refers to the ability of the membrane to detect even small amounts of bound or attached species. "Specificity" means the ability of the membrane to selectively bind or filter certain species from complex mixtures.

A practical advantage of the present invention is that membranes can be produced that are reactive enough to react with typical nucleophiles such as amines but not so reactive that they suffer degradation by ambient moisture or oxygen. Thus, one aspect of the invention provides a membrane which has not only a high binding capacity and improved sensitivity but also a prolonged shelf life and ease of handling.

In one aspect, the membrane of this invention is polymeric and microporous, i.e., it includes a polymer and has an internal surface and an external surface. When the activated microporous membrane of the invention is contacted with a mixture that is to be filtered, the external portion of the membrane is immediately and directly exposed to the mixture. But the internal surface or interstices of the membrane are not immediately exposed. It is only after the membrane has been in contact with the mixture for a period of time that the internal surface is exposed to the mixture. These internal interstices or pore surfaces are collectively termed the "internal surface" of the membrane. This internal surface area has been found to be important to the success of the invention.

In one aspect, the activated membranes of this invention have a plurality of aldehyde functional groups substantially covering the internal and external surfaces. The interstices as well as the external surfaces are covered by an effective amount of aldehyde for activating the membrane. The number of aldehyde groups is sufficient for effective covalent bonding with amine containing materials and other aldehyde reactive groups.

The following detailed description describes the claimed invention in greater detail and discloses a preferred embodiment. The description, along with the examples and the rest of this disclosure, is addressed specifically to those skilled in the art, to enable them to make and to use the claimed invention.

DETAILED DESCRIPTION AND PREFERRED EMBODIMENT

As discussed above, the invention is broadly directed to a blotting composition which includes a substrate which is applied to an activated microporous membrane that comprises a membrane polymer and a polyaldehyde. The polyaldehyde is physically combined with the membrane polymer in an amount sufficient to activate the membrane, i.e., to provide for effective covalent bonding by amine containing materials and other aldehyde reactive materials.

"Activating" or "combining" in this sense is a broad term that encompasses both (a) coating or treating a precast microporous membrane with the polyaldehyde; and (b) physically mixing the polyaldehyde with the membrane polymer before casting the membrane. The former is called "membrane post treatment" while the latter is called "precasting." "Physically combining" or "physically mixing" the polymer and the polyaldehyde means that there is a lack of significant chemical reaction between the polyaldehyde and the polymer.

In one aspect, the invention comprises a blotting composition which includes an activated microporous membrane in which substantially all the available surfaces of the membrane are coated by the polyaldehyde. The activated membrane thus contains sufficient polyaldehyde to provide effective aldehyde functionality on substantially all available surfaces, i.e., both the external and internal surfaces. The resulting free aldehyde groups covering substantially all exposed surface areas provide effective covalent bonding between the finished membrane of this invention and aldehyde reactive materials, such as amines, which contact the membrane.

The membrane of the present invention may be a "supported" membrane or an unsupported membrane. A supported membrane is a membrane cast on a substrate, preferably a nonwoven fabric. Supported membranes are often considered to have better mechanical properties and ease of handling than unsupported membranes.

Generally, to form the membrane of the present invention, the polyaldehyde is dissolved in a solvent to form a mixture. The mixture is then physically combined with the membrane polymer by either membrane post treatment or precasting. After the activated microporous membrane is made, the solvent is generally removed by washing, although some residual solvent may remain.

In certain embodiments, the polyaldehyde mixture is concentrated enough to properly activate the membrane. The membrane material, on the other hand, is sturdy and of sufficient chemical resistance to remain porous and substantially undamaged by the polyaldehyde containing mixture.

Membrane Post Treatment

In a preferred aspect, the microporous membrane is first cast from the membrane polymer, then activated by physically coating or treating the cast membrane with the polyaldehyde containing mixture. This physical combination does not include any significant chemical reaction, such that would cause potential damage to the pore structure.

Polyaldehydes in general are contemplated for use in this invention. Preferably, the polyaldehyde chosen will be sufficiently soluble in the solvent to provide a true solution to avoid, for example, undesirable dispersions which could cause ineffective coating of the membrane surfaces. Polyaldehydes which have been found especially useful in the practice of the invention include polyacrolein and acrolein copolymers.

It has been found that the concentration of the solvent, in which the polyaldehyde dissolves, is important. If the solvent is not concentrated enough, it will not form a true solution with the polyaldehyde. If the solvent is too concentrated, it could damage the membrane pore structure of certain membranes. Accordingly, the solvent concentration should be reduced to avoid damaging the membrane. This can be done by diluting the solvent concentration with, for example, water or alcohol, which will reduce the solvent concentration yet still dissolve the polyaldehyde.

Where polyacrolein is employed, a strong solvent such as pyridine or dimethyl formamide (DMF) is used to dissolve the polyacrolein. One embodiment of the post treatment mode comprises a microporous membrane treated with pure polyacrolein dissolved in DMF or pyridine. At high concentrations DMF or pyridine damages the pore structure of polysulfone. Accordingly, for polysulfone, an effective DMF solution in a polyacrolein containing mixture has about 60 percent DMF and about 40 percent water. Example 6 shows one operative range of DMF solvent concentrations. Other membrane polymers, such as those made from nylon or polypropylene, are generally not sensitive to pore damage and can be successfully coated with polyacrolein without regard to the solvent concentration.

One polyaldehyde which has been found to work well with polysulfone membranes is a copolymer of acrolein, e.g., hydroxyethyl methacrylate acrolein copolymer. This copolymer is more soluble in solvents such as DMF and pyridine than is pure polyacrolein. Thus a less concentrated solvent can be used to avoid any potential damage to the membrane pore structure.

The proportionate amounts of polyaldehyde and solvent are also important. Enough polyaldehyde should be present to sufficiently activate the membrane. Further, enough solvent must be employed to dissolve the polyaldehyde. It is contemplated that from about 0.2 weight percent to about 10 weight percent polyaldehyde per volume of solution is adequate.

Precasting Treatment

Another embodiment provides for the activation of the membrane polymer prior to casting. This may be referred to as the precasting treatment. In this embodiment, the polyaldehyde and the membrane polymer are physically mixed before casting. There should be sufficient polyaldehyde to activate the membrane polymer. With polyacrolein, weight ratios of from about 1:5 to about 1:1 polyacrolein to membrane polymer are appropriate.

The invention is not strictly limited to a particular species of microporous membrane. However, selection of an appropriate membrane polymer is important to achieve maximum effectiveness. Generally speaking, the species of membrane polymer must be able to withstand the solvent system that comprises the polyaldehyde. Examples of suitable membrane polymers include polysulfone and polyacrylonitrate-vinyl chloride copolymer. Other membranes, such as nylon, cellulose acetate, polyvinylidene fluoride, polypropylene, and glass fibers, could also be expected to work.

Membrane materials which would swell or dissolve from contact with the polyaldehyde containing mixture are undesirable. However, this depends to some extent on the concentration of the solvent used for the polyaldehyde. For example, concentrated DMF on a polysulfone membrane causes damage to the membrane. Consequently, it is preferable to use a more soluble polyaldehyde such as a copolymer of acrolein and hydroxyethyl methacrylate with polysulfone microporous membrane. No significant damage of polysulfone membrane pore structure has been encountered with this copolymer solvent system.

Polymerization

Polymerization conditions are also important. For example, under certain conditions polymerization will involve the aldehyde group of acrolein, and the resulting polymer will therefore have very little, if any, aldehyde functionality.

Where a polyaldehyde copolymer is formed between an acrolein monomer and hydroxyethyl methacrylate, free radical copolymerization is preferred, using a proper conventional initiator such as peroxide. In contrast, if the reaction is done under the influence of base-catalyzed initiators, such as sodium hydroxide, few if any free aldehydes are formed. Likewise, if ionizing radiation is used, microspheres will be formed, which may not be able to penetrate all interstices of the porous membrane.

Generally, the preferred polymerization conditions are those which provide a highly soluble and highly functional polymer mixture that will cover the microporous membrane efficiently and without damage to or clogging of the pore structure. The polyaldehyde of the present invention is soluble enough in solutions having solvents such as DMF or pyridine to penetrate substantially all pores or interstices of the microporous membrane structure.

In one embodiment of this invention, the aldehyde functional groups are attached by admixing the membrane polymer with an effective amount of the polyaldehyde-containing mixture. Generally speaking, the type and amount of polyaldehyde containing mixture vary the binding effectiveness of the membrane. These are discussed below.

A preferred embodiment which has good solubility but which does not damage the pore structure of a polysulfone membrane is an acrolein copolymer. However, incorporation of a comonomer with acrolein may somewhat reduce the concentration of the reactive aldehyde groups. Accordingly, selection of the comonomer is important. A good balance of solubility and high reactivity is found with the copolymers of acrolein and hydroxyethyl methacrylate.

Process for Making the Membrane

Another broad aspect of the invention is the process for making the activated microporous membrane, which basically comprises an activating step and a casting step. More particularly, the activating step refers to activating the membrane polymer by mixing, treating or combining a polyaldehyde with the membrane polymer. The casting step comprises casting the microporous membrane itself which includes the membrane polymer.

The actual method for casting microporous membranes is conventional. In the preferred embodiment, the casting step is performed first. Here, the microporous membrane matrix is cast from a membrane polymer system, which may include polymers such as polysulfone, polyacrylonitrilevinyl chloride, nylon, polyvinylidene fluoride and polypropylene. The matrix may also include glass fibers. Preferably, the pore sizes of the microporous membrane are between about 0.1 and about 10 microns in diameter. These have been found sufficiently porous for most applications.

After the casting of the membrane, the activating or treating step is performed. Here, the polyaldehyde is physically combined with the cast microporous membrane. Preferably, a dilute solution of the polyaldehyde containing mixture is made in a solvent that is not harmful to the membrane polymer system. A harmful solvent is generally one that would increase the solubility of the membrane to a point where it would damage the membrane by causing the pore structure to collapse. As discussed above, the preferred solvent is an aqueous DMF solution having at most about 60% DMF. Pyridine may also be used as a solvent.

One of the embodiments includes copolymerizing acrolein with hydroxyethyl methacrylate to obtain a copolymer, then mixing with a solvent to obtain a mixture having the appropriate concentration and solubility. The membrane is dipped in this mixture in a manner ensuring proper wetting of all surfaces, internal and external. Once dried, the membrane is ready for use.

In another embodiment of this process, the activating step is performed first. In this embodiment, the polyaldehyde is physically mixed with the microporous polymer prior to casting. A polyaldehyde containing mixture is physically mixed with a membrane polymer in the proper proportions. Using this mixture, a membrane matrix is cast in a conventional manner. When the membrane has undergone transition from a liquid or sol phase to a solid or gel phase and subsequently dried, the pore surfaces of the membrane will have aldehyde functionalities available for reaction.

The following reaction steps illustrate how acrolein is polymerized. As indicated, acrolein can be polymerized either through the aldehyde group or the carbon-carbon double bond, depending on polymerization conditions.

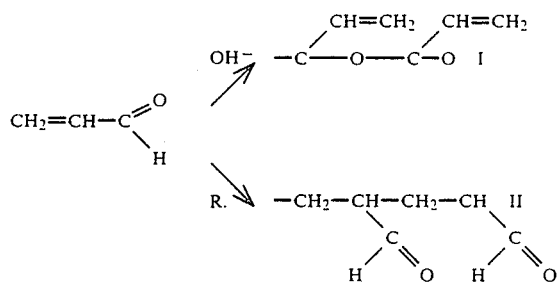

The resulting polymer is therefore one having either pendant vinyl (I) or aldehyde (II) groups. Polymer II is suitable for a cast membrane in the presence of a solvent system or alternatively for blending in a membrane forming mix so as to activate the membrane before casting. As discussed above, it is preferable to improve the solubility of the aldehyde polymer so that a larger variety of membranes can be treated.

The activated microporous membrane can be used in a variety of applications. It is particularly effective as a binding matrix. Various amine containing macromolecules will attach to it covalently. The membrane can therefore be used for selectively binding proteins, nucleic acids and other nucleophiles. The bound species can then be used in a variety of uses such as catalysis and analysis.

Blotting Compositions

In another broad aspect, the invention involves a blotting composition and a method for blotting involving a polyaldehyde-activated, microporous membrane. "Blotting" refers to the well-known technique for analyzing specific gene structures. DNA blotting is a step in the procedure known as the "Southern Transfer," which was pioneered by E. M. Southern in 1975. Blotting also refers to RNA-blotting (Northern Transfer) and protein/immunological blotting (Western Transfer).

The blotting composition of the invention comprises a substrate, preferably a gel, applied to an activated membrane, which is preferably microporous. The substrate may include various macromolecules, such as proteins or nucleic acids, e.g., DNA or RNA. The membrane comprises an activated membrane polymer, i.e., one having a sufficient amount of a polyaldehyde-containing mixture to provide for effective covalent bonding with amine-containing materials and other aldehyde reactive materials which may contact the membrane. A membrane meeting this description is discussed above.

In a more specific aspect, the invention is directed to a composition comprising a sample of nucleic acid contacted, and preferably directly applied, to the outside surface of the membrane by spot wetting. Use of this composition provides a means of detecting the specific sequence of the membrane-bound nucleic acid via hybridization to the bound specie.

Various methods are available for applying a substrate to a membrane, such as spot-wetting or dot-blotting. The "dot-blot" method is useful for detecting a specific nucleic acid sequence. The method may comprise hybridizing the membrane-bound nucleic acid with a probe-attached, nucleic acid strand which is complementary only to the specific sequence of the nucleic acid. This probe-attached, nucleic acid strand generally binds or hybridizes efficiently only to the membrane-bound nucleic acid molecules which contain the specific sequence. Upon hybridizing the nucleic acid, the probe may be detected by a standard enzyme-linked immuno sorbent assay (ELISA). Example 11 illustrates an aspect of the invention involving a DNA dot-blot procedure using a polyaldehyde-activated, polysulfone membrane.

Macromolecule and Bacteria Transfer and Identification

Another aspect of the invention resides in transferring biological samples of bacteria or macromolecules such as DNA, RNA, and protein to an immobilizing matrix, specifically a microporous membrane comprising a membrane polymer and an activating amount of polyaldehyde. Preferably, polyaldehyde is present in an amount sufficient to bind or immobilize the macromolecule or bacteria.

Accordingly, a specific embodiment of the invention is directed to a dot-blot method, whereby specific sequences of nucleic acid in a biological sample may be detected. The method comprises applying by spot-wetting a biological sample which includes the nucleic acid in question to the microporous membrane. Normally, a bacterial cell from the biological sample is lysed to release the macromolecule, DNA, or protein. After the biological sample has been applied, the nucleic acid is hybridized with a probe-attached, nucleic acid strand which is complementary to the specific sequence of the nucleic acid sought to be detected. After hybridization, the probe is detected by a standard radioactive probe or a procedure known as enzyme linked immuno sorbent assay or "ELISA." Preferably, prior to the hybridization step, the non-specific reactive sites on the membrane are blocked or "capped" by, e.g., reacting the membrane with a solution of 2% w/v non-fat dry milk/2% w/v glycine in phosphate buffered solution.

Another specific embodiment of the invention is directed to a method for identifying specific nucleic acid sequences comprising separating polydispersed, biological samples or macromolecules, e.g., nucleic acids, into fractions according to their size and charge by gel electrophoresis; transferring the samples or the macromolecules to the microporous membrane; and identifying the specific nucleic acid sequence. The general procedure for doing this is well-known in the art as Southern Transfer (for DNA molecules), Northern Transfer (for RNA molecules), and Western Transfer (for proteins). In a more specific aspect, the invention comprises a method for identifying DNA sequences comprising transferring a specific DNA, e.g., sonicated salmon DNA, from an agarose gel disk onto a polyaldehyde-activated, polysulfone microporous membrane using sodium citrate buffer with an appropriate electrical current running through the gel; and detecting the membrane-bound DNA using ELISA or a standard radioactive probe detection procedure.

In another specific aspect, the invention is directed to a method for identifying specific nucleic acid sequences and proteins comprising transferring the nucleic acids to the microporous membrane by capillary action and thereafter detecting the sequence. Detection of the sequence can be carried out by e.g., ELISA. A more specific embodiment comprises transferring sonicated salmon DNA from an agarose gel disk onto a polyaldehyde activated microporous polysulfone membrane using sodium citrate buffer by capillary action using absorbent paper.

Electrophoresis

Another aspect of the invention is directed to gel electrophoresis. Generally speaking, gel electrophoresis is useful for separating, quantitating and characterizing macromolecules such as proteins. It is also useful for separating poly-dispersed nucleic acid samples into fractions according to their size and charge.

Before identifying specific nucleic acid sequences, poly-dispersed samples of nucleic acid may be separated into fractions, according to their size and charge, by conventional gel electrophoresis. After this separation, each fraction is transferred from the gel to a solid support, usually either by capillary action or electrical potential. This transfer procedure is commonly known as "Northern Transfer" for RNA and "Southern Transfer" for DNA. After this transfer, detection of the nucleic acids or proteins which are bound to the microporous membranes and which have specific sequences or particular immunological characteristics may be carried out by standard hybridization methods as described above such as gel blotting, spot-wetting or the dot-blot method.

Accordingly, in one aspect, the invention is directed to a gel electrophoresis method, comprising transferring a macromolecule such as a protein or nucleic acid to an activated microporous membrane which comprises a membrane polymer and a polyaldehyde such as the polyaldehyde-containing membrane described in other parts of this detailed description. Transfer of nucleic acid or proteins from a gel by electrical and capillary actions onto a polyaldehyde activated membrane in accordance with the present invention and identification of specific nucleic acid sequences are exemplified in Examples 12 and 13.

The invention will be further clarified by a consideration of the following examples, which are intended to be purely exemplary of the use of the invention.

EXAMPLES

Example 1

Polymerization of Acrolein

A mixture containing freshly distilled acrolein (50 ml, 0.749 moles), benzoyl peroxide (2 g, 8.26 millimoles) and 250 ml of dimethyl formamide (DMF) was purged for 3 hours with nitrogen at room temperature. Then the mixture was heated to 70°–80° C. for 2 hours with stirring. The resulting solution was stirred at room temperature for 15 hours. A yellowish homogeneous solution was obtained. This solution was diluted with water to obtain polyacrolein as a white precipitate. Polyacrolein was redissolved in pyridine and stored at room temperature for use in Example 2.

Example 2

Activation of a Membrane By Coating a Polysulfone Microporous Membrane with Polyacrolein Mixture The polyacrolein/pyridine solution of Example 1 was heated to 70° C. and diluted with 1 volume of boiling water. This polyacrolein containing mixture was applied on a polysulfone microporous membrane at 70° C. and dried at room temperature in air. No sign of clearing (destruction of porous structure) of the membrane was observed by the above treatment. This indicated that the mixture solvent was not too strong.

Example 3

Activation of a Membrane by Precasting with a Polyacrolein Mixture

The polyacrolein/DMF solution in Example 1 was mixed with polysulfone to precast a microporous membrane. The casting mix was prepared by blending 30 g of the polyacrolein solution, 10 ml of additional DMF, 10 g of polyethylene glycol, 1.5 g of polyvinyl pyrrolidinone, and 8.5 g of polysulfone. The mix was cast on a glass plate at room temperature and stored in a humidity chamber to cause pore formation. The microporous membrane produced by this method exhibited a water flow rate of 6.8 sec/100 ml/9.62/572 Hg and a water bubble point of 18 psi. This indicated that the membrane was microporous and possessed an adequate pore structure.

Example 4

Copolymerization of Acrolein and Hydroxyethyl Methacrylate

Hydroxyethyl methacrylate acrolein copolymer was dissolved in DMF and diluted with water. One such mixture was made in the following manner. A mixture consisting of freshly distilled acrolein (50 ml, 0.749 moles), hydroxyethyl methacrylate (15 ml, 0.12 moles), benzoyl peroxide (3.25 g, 13.4 moles) and 200 ml of DMF was purged with nitrogen for 1 hour and then refluxed for 1 hour. The resulting mixture was stirred at room temperature for 15 hours. A yellow copolymer solution was obtained. This copolymer solution was diluted with 1.5 volume of water without any solidification.

Example 5

Activation of a Polysulfone Membrane By Coating a Microporous Membrane with a Copolymer Mixture The copolymer solution of Example 4 was heated to 70° C. and diluted with 1.5 volumes of water at 70° C. This copolymer solution was applied on a supported microporous polysulfone membrane at room temperature and dried in air at room temperature. No sign of clearing of the membrane was observed by this treatment. Further, the supported polysulfone membrane exhibited a water flow rate of 13.5 sec/100 ml/9.62/572 Hg after the above treatment. This indicated that the hydroxyethyl methacrylate acrolein copolymer mixture did not significantly damage the pore structure of the microporous membrane.

Example 6

Copolymerization of Acrolein and Hydroxyethyl Methacrylate

In order to demonstrate the usefulness of this invention with different membranes, a second copolymer mixture was made and applied to a polysulfone microporous membrane and an acrylonitrile/vinyl chloride copolymer microporous membrane.

First, a mixture of freshly distilled acrolein (265 ml, 3.97 moles), hydroxyethyl methacrylate (62 ml, 0.49 moles), benzoyl peroxide (17 g, 70 moles) and DMF (1060 ml) was purged with $N_2$ gas for 6 hours. This mixture was then heated to 95° C. for 22 hrs. The final concentration of the copolymer was 17.5% (w/v). A brown copolymer solution was stored at room temperature for membrane post treatment.

Example 7

Activation of Polysulfone and Polyacrylonitrile-Vinyl Chloride Microporous Membranes by Coating The copolymer solution in Example 6 was diluted with a mixture of 1:1:1 DMF/water/isopropanol to form various copolymer solutions including 0.5%, 1%, 2%, 3%, 4% and 5% (w/v) solutions. These copolymer solutions were applied to a polysulfone microporous membrane and a polyacrylonitrile-vinyl chloride membrane.

The membranes were quenched in deionized water, washed a few times with deionized water, and dried at 70° C. The flow rates of two of the membranes, i.e., those treated with the 4% solution, were measured. It was found that the water flow rates of the membranes were reduced. For instance, the flow rate of the treated polysulfone membrane was reduced from 10.7 sec/100 ml/9.62 cm$^2$/572 mm Hg to 13.1 sec/100 ml/9.62 cm$^2$/572 mm Hg. This reduction in flow rates indicated that the internal surfaces of the membranes were coated. The flow rates of the treated membranes are found in Table 1. The binding capacities of these membranes are shown in Example 8.

TABLE 1

| Water Flow Rates of Composite Membranes | |
|---|---|
| Membrane | Water Flow Rate sec/100 ml/9.2 cm$^2$/ 572 mm Hg |
| Polysulfone membrane coated with aldehyde polymer in Example 7. | 13.1 |
| Acrylonitrile/vinyl chloride copolymer supported membrane coated with aldehyde polymer in Example 7. | 16.6 |

Example 8

As demonstrated by the following data, several embodiments of this invention showed excellent binding capacities.

TABLE 2

| Total Protein Binding Capacity (ug/cm$^2$) of the Membranes by ELISA | |
|---|---|
| Membrane | Total Binding Capacity (ug/cm$^2$) |
| Polysulfone membrane coated with aldehyde polymer in Example 7. | 96 |
| Acrylonitrile/vinyl chloride copolymer supported membrane coated with aldehyde polymer in Example 7.[a] | 106 |

[a] 2¼ hr. binding time at 35° C.

Example 9

Another embodiment of the invention comprising glyoxyl agarose polyaldehyde, was made to demonstrate the further usefulness of the invention. A solution was prepared, mixing 0.5 g glyoxyl agarose (NuFix ™ manufactured by FMC Corporation) in 200 ml of boiling water. The solution was used to treat a polysulfone membrane in the same manner as in Example 5. It was observed that the flow properties of the membrane remained unchanged indicating that the pore structure remained essentially undamaged.

Example 10

As demonstrated by the following data, the membranes of this invention showed specificity and binding capacity that was superior to other commercially available membranes. Commercial Affinity Membrane A was a nylon-based membrane sold by Pall Corporation under the name Biodyne. Commercial Affinity Membrane B was a polyvinylidene difluoride-based membrane sold by Millipore Corp. under the name Immobilon.

TABLE 3

| Total Binding Capacities (ug/cm$^2$) of Membranes by BCA Method (Total binding capacity = covalent or permanently bound protein + loosely bound or noncovalent bound protein per cm$^2$) | | |
|---|---|---|
| Membrane | Total Binding Capacity (ug/cm$^2$) | Non-Covalently Bound Protein (ug/cm$^2$) |
| Commercial Affinity Membrane A | 57 | 10 |
| Commercial Affinity Membrane B | 42 | Not Detectable (10) |
| Nitrocellulose[a] | 94 | 64 |
| Polysulfone Membrane Coated with Aldehyde Polymer, from Example 5[b] | 120 | Not Detectable (10) |
| Polysulfone/Aldehyde Polymer Microporous Membrane in Example 7[a] | 90 | Not Detectable (10) |
| Polysulfone Supported Membrane Coated with Aldehyde Polymer in Example 7[b] | 125 | 5.2 |
| Polysulfone Membrane Coated with Aldehyde Polymer in Example 7[b] | 148 | 3.4 |
| Polysulfone Membrane Coated with Aldehyde Polymer in Example 2[d] | 87 | |

[a] 1 hour binding time at room temperature.
[b] 1 hour binding time at 60° C.
[c] 3 hours binding time at room temperature.
[d] 3.45 hours binding time at room temperature.

These binding capacities were determined according to the BCA method, developed by P. K. Smith, et. al., *Analytical Biochemistry*, 150, page 76 (1985).

Example 11

This example shows the utility of the invention as it relates to a polyaldehyde activated polysulfone membrane for a DNA dot-blot procedure. Typically, sonicated salmon DNA is used as a carrier DNA. Here, however, it is being used to exemplify the present invention. Four 1-μl solutions of sonicated salmon DNA (single stranded, 580 bases) having, respectively, 0, 5, 50 and 500 ng of DNA were applied to four polyaldehyde activated polysulfone membranes. Excess binding sites on the membranes were capped by reacting the membranes with a 2% w/v non-fat dry milk/2% w/v glycine in phosphate-buffered saline. The membranes were then exposed to a prehybridization solution hybridized with the sulfoprobe-attached complementary DNA standards according to the procedures outline in T. Maniatis, *Molecular Cloning—A Laboratory Manual*, Cold Spring Harbor Laboratory (1982), which is hereby incorporated by reference. Detection of sulfoprobe was carried out by the procedure described in Technical Bulletin No.: Probe-2 (6-87), Sigma Chemical Co. (1987). The resulting color products, i.e., dots, were quantitated on a densitometer at 570 nm. It was found that for the membranes having 0, 5, 50 and 500 ng amount of DNA applied, the detection of DNA as the intensity of dots ($OD_{570}$), respectively, were 0.018, 0.089, 0.164, and 0.288.

Example 12

This example shows the utility of the invention as it relates to the electro-transfer of DNA to polyaldehyde activated polysulfone membranes. Sonicated salmon DNA (single stranded, 580 bases) was transferred from 1% agarose gel disks onto membranes using a sodium citrate buffer at 200 MA of electrical current for two hours. The gel disks has diameters of 13 mm, and thicknesses of 0.13 mm; and employed a 1% agarose in sodium citrate buffer and 200 ng of DNA per gel disk. Three layers of 24 mm membrane disks were used in the transfer to observe the membrane's ability to stop the nucleic acid.

After the electro-transfer, these membranes were treated with 2% w/v glycine/phosphate buffer saline to deactivate the excess binding cites. Detection of the membrane-bound DNA was carried out using the procedure described in Example 11.

A purple-blue-colored 13 mm circle on a white background was observed for the first layer of polyaldehyde activated polysulfone membrane. The second and third layers showed no color, suggesting that nucleic acid molecules did not penetrate through the first layer.

Example 13

This example shows the utility of the invention as it relates to the capillary-transfer of DNA to polyaldehyde activated polysulfone membranes. Sonicated salmon DNA (single stranded, 580 bases) was transferred from 1% agarose gel disks onto polyaldehyde activate polysulfone membranes using sodium citrate buffer by capillary action, using absorbent paper, for 15 hours. Each agarose gel disk was 13 mm in diameter and 0.13 mm thick, employing 1% agarose in sodium citrate buffer and 200 micrograms of DNA per gel disk. Three layers of 24 mm membrane disks were used in the transfer in order to observe the membrane's ability to stop the nucleic acid. After the transfer, the membranes were treated generally as in Example 11 to detect membrane-bound DNA.

A purple-blue colored 13 mm circle on a white background was observed for the first layer of polyaldehyde activated polysulfone membrane. The second and third layers showed no color, suggesting that nucleic acid molecules did not penetrate through the first layer.

Naturally, other embodiments and methods, improvements and modifications are included within the scope of the invention which have not been discussed in detail. For example, a procedure for transferring macromolecules may involve contacting the biological sample onto a microporous membrane which comprises a polyaldehyde mixed with compatible membrane polymer other than polysulfone, e.g., nylon or polypropylene. Alternatively, the procedure may include additional steps, such as applying a vacuum to the membrane to improve the filtration of the sample so that the macromolecules are bound to the membrane in a shorter time than if no vacuum were applied. Likewise, the procedure may include various prehybridization steps to improve the specificity of the nucleic acid binding to the membrane. It is understood, however, that the invention is not limited to the embodiments and examples discussed above. The invention is defined by looking to the claims, found below.

What is claimed is:

1. A blotting composition, comprising a substrate applied to an activated microporous membrane comprising a membrane polymer and having (1) an internal surface comprising interstices or pore surfaces and (2) an external surface;
   wherein substantially all said surfaces of the microporous membrane are coated without significant chemical reaction to substantially all said available surface areas of said microporous membrane and thereby activated by a polyaldehyde-containing mixture in an amount sufficient to effectively activate the microporous membrane; and
   wherein the mixture is soluble enough to penetrate substantially all said interstices of the microporous membrane without substantial damage to the pore structure.

2. The blotting composition as recited in claim 1, wherein the substrate is a gel.

3. The blotting composition as recited in claim 1, wherein the substrate is a gel comprising macromolecules selected from the group consisting of DNA, RNA, and proteins.

4. The blotting composition as recited in claim 1, wherein:
   the substrate is a gel which comprises macromolecules electrophoretically separated into a series of bands; and
   the gel additionally comprises a dye that binds to the macromolecules.

5. The blotting composition as recited in claim 1 wherein the substrate comprises materials capable of being bound to the polyaldehyde-containing mixture.

6. The blotting composition as recited in claim 5 wherein said materials comprise amine-containing materials.

* * * * *

UNITED STATES PATENT AND TRADEMARK OFFICE
CERTIFICATE OF CORRECTION

PATENT NO. : 4,992,172

DATED : February 12, 1991

INVENTOR(S) : Kariyawasam P. W. Pemawansa, et al.

It is certified that error appears in the above-identified patent and that said Letters Patent is hereby corrected as shown below:

Column 10, line 17, "sec/100 ml/9.62/572 Hg" should be --sec/100 ml/9.62 cm$^2$/572 Hg--;

Column 10, line 48, "sec/100 ml/9.62/572 Hg" should be --sec/100 ml/9.62 cm$^2$/572 Hg--;

Column 13, line 16, "24 mm" should be --24-mm--;

Column 13, line 41, "24 mm" should be --24-mm--.

Signed and Sealed this

Twenty-first Day of July, 1992

Attest:

DOUGLAS B. COMER

Attesting Officer     Acting Commissioner of Patents and Trademarks